United States Patent
Litt et al.

(10) Patent No.: US 9,420,953 B2
(45) Date of Patent: Aug. 23, 2016

(54) METHOD FOR IMPLANTING FLEXIBLE AND SCALABLE SENSOR ARRAYS INTO PATIENT TISSUES

(71) Applicant: The Trustees of the University of Pennsylvania, Philadelphia, PA (US)

(72) Inventors: Brian Litt, Bala Cynwyd, PA (US); Jonathan Viventi, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 14/795,745

(22) Filed: Jul. 9, 2015

(65) Prior Publication Data

US 2015/0305625 A1 Oct. 29, 2015

Related U.S. Application Data

(62) Division of application No. 12/921,808, filed as application No. PCT/US2009/036956 on Mar. 12, 2009, now Pat. No. 9,107,592.

(60) Provisional application No. 61/035,909, filed on Mar. 12, 2008.

(51) Int. Cl.
*A61N 1/00* (2006.01)
*A61B 5/00* (2006.01)
(Continued)

(52) U.S. Cl.
CPC .......... *A61B 5/0084* (2013.01); *A61B 5/04* (2013.01); *A61B 5/14503* (2013.01);
(Continued)

(58) Field of Classification Search
CPC ..... A61N 1/05; A61N 1/0553; A61N 1/0531; A61N 1/0534; A61B 2562/02; A61B 2562/0209; A61B 2562/028; A61B 2562/0285; A61B 2562/164; A61B 2562/046; A61B 5/04; A61B 5/04001; A61B 5/0402; A61B 5/0408
See application file for complete search history.

(56) References Cited

U.S. PATENT DOCUMENTS

| | | |
|---|---|---|
| 4,735,208 A | 4/1988 | Wyler et al. |
| 4,969,468 A | 11/1990 | Byers et al. |

(Continued)

FOREIGN PATENT DOCUMENTS

| | | |
|---|---|---|
| WO | WO 2003-041795 | 5/2003 |
| WO | WO 2006-029090 | 3/2006 |

OTHER PUBLICATIONS

Ad-Tech® Medical Instrument Corporation, http://www.adtechmedical.com, 1985-2015, 2 pages.
(Continued)

*Primary Examiner* — Mallika D Fairchild
(74) *Attorney, Agent, or Firm* — Baker & Hostetler, LLP

(57) ABSTRACT

An implantable sensor array incorporates active electronic elements to greatly increase the number of sensors and their density that can be simultaneously recorded and activated. The sensors can be of various configurations and types, for example: optical, chemical, temperature, pressure or other sensors including effectors for applying signals to surrounding tissues. The sensors/effectors are arranged on a flexible and stretchable substrate with incorporated active components that allow the effective size, configuration, number and pattern of sensors/effectors to be dynamically changed, as needed, through a wired or wireless means of communication. Active processing allows many channels to be combined either through analog or digital means such that the number of wires exiting the array can be substantially reduced compared to the number of sensors/effectors on the array.

19 Claims, 17 Drawing Sheets

(51) Int. Cl.
*A61B 5/04* (2006.01)
*A61N 1/05* (2006.01)
*A61B 5/145* (2006.01)
*A61N 5/06* (2006.01)

(52) U.S. Cl.
CPC ............... *A61B 5/6852* (2013.01); *A61N 1/05* (2013.01); *A61N 1/0553* (2013.01); *A61N 5/0601* (2013.01); *A61B 5/0031* (2013.01); *A61B 2562/02* (2013.01); *A61B 2562/028* (2013.01); *A61B 2562/0209* (2013.01); *A61B 2562/0233* (2013.01); *A61B 2562/046* (2013.01); *A61B 2562/164* (2013.01); *A61N 1/0531* (2013.01); *A61N 1/0534* (2013.01)

(56) References Cited

U.S. PATENT DOCUMENTS

| | | | |
|---|---|---|---|
| 5,215,088 A | | 6/1993 | Normann et al. |
| 5,411,551 A | * | 5/1995 | Winston ............... A61F 2/92 600/347 |
| 5,531,779 A | | 7/1996 | Dahl et al. |
| 5,961,909 A | * | 10/1999 | Iverson ............... A61B 5/0422 264/219 |
| 6,024,702 A | | 2/2000 | Iversen |
| 6,032,062 A | | 2/2000 | Nisch |
| 6,097,984 A | | 8/2000 | Douglas |
| 6,301,500 B1 | | 10/2001 | Van Herk et al. |
| 6,666,821 B2 | | 12/2003 | Keimel |
| 6,807,439 B2 | | 10/2004 | Edwards et al. |
| 7,935,056 B2 | | 5/2011 | Zdeblick |
| 2003/0113832 A1 | | 6/2003 | Lauf |
| 2004/0006264 A1 | | 1/2004 | Mojarradi |
| 2004/0193232 A1 | | 9/2004 | Yagi et al. |
| 2004/0200734 A1 | | 10/2004 | Co et al. |
| 2006/0129056 A1 | | 6/2006 | Leuthardt et al. |
| 2007/0185537 A1 | | 8/2007 | Zdeblick |

OTHER PUBLICATIONS

Aziz et al, "256-Channel Integrated Neural Interface and Spatio-Temporal Signal Processor", Circuits and Systems, ISCAS 2006, Proceedings 2006 IEEE International Symposium on May 21-24, 2006, 4 pages.

EP Patent Application No. 09 721 084.3: Office Action dated Mar. 19, 2014, 4 pages.

International Application No. PCT/US2009/036956: International Search Report dated Jun. 29, 2009.

Nordhausen et al, "Single Unit Recording Capabilities of a 100 Microelectrode Array", Brain Research, 726(1-2), Jul. 8, 1996, 129-140.

Pakkenberg, B., and Gundersen, HJ, "Neocortical Neuron Number in Humans: Effect of Sex and Age", Journal of Comparative Neurology, 384(2), 312-320.

Patterson et al, "A Microelectrode/Microelectronic Hybrid Device for Brain Implantable Neuroprosthesis Applications", IEEE Transactions on Biomedical Engineering, Oct. 2004, 51(10), 1845-1853.

* cited by examiner

METHOD FOR IMPLANTING FLEXIBLE AND SCALABLE SENSOR ARRAYS INTO PATIENT TISSUES

CROSS REFERENCE TO RELATED APPLICATIONS

This patent application is a Divisional of U.S. patent application Ser. No. 12/921,808, filed Nov. 12, 2010, which claims priority to International Patent Application No. PCT/US2009/036956 filed Mar. 12, 2009, which in turn claims benefit of U.S. Provisional Application No. 61/035,909 filed Mar. 12, 2008.

FIELD OF THE INVENTION

The present invention relates to a biological sensor/effector (e.g. stimulation) array that is manufactured using flexible and stretchable active electronics so as to better conform to the natural shape of the brain, peripheral and cranial nerves, heart, blood vessels, spinal cord and other biological structures, and have a higher density of sensors than is possible with current electrode array technology. The integration of active electronics also allows for dynamic sensor/effector reconfigurability for scalable sensing and integrated patterned stimulation.

BACKGROUND OF THE INVENTION

There is a great need for flexible, multi-scale, configurable sensor/effector systems that can be cut to specific sizes and shapes and adapted "on the fly" to adjust to specific temporal and spatial recording scales in the body. A driving motivation for such technology is the rapidly growing awareness that brain, cardiac and other biological recordings must be made multi-scale, spanning from individual and multiple unit (cell) activities to large-scale field potentials, depending upon the application. These sensor systems must also be capable of both recording and modulating tissue function, as part of new diagnostic and therapeutic devices for neurological and other diseases, brain and other tissue injury, and acquired conditions.

Taking an example from the brain-computer interface technologies, the current state of the art for flexible subdural grid electrodes for localizing seizures in the human brain typically utilize ~4 mm platinum-iridium or stainless steel contacts spatially separated by 10 mm. Such electrodes are available from Ad-Tech Medical Instrument Corporation (http://www.adtechmedical.com). As illustrated in FIG. 1, a long-term monitoring (LTM) subdural grid 10 of this type containing 16 contacts 20 has a separation of 10 mm between each contact 20, and 1 or 2 "tails" 30 that contain contacts 40 for output of electrical signals that correspond to each contact 20 on the subdural grid (each contact 20 on the subdural grid has an individual wire attached to it, which is connected to a contact 40 in one of the "tails.") Similar electrodes are illustrated in U.S. Pat. No. 4,735,208, entitled "Subdural strip electrodes for determining epileptogenic foci." However, these electrodes are not effective for detecting all signals of interest in the brain, for example, due to their large size and large spacing between contacts.

The choice of the particular sizing and spacing of the electrodes is partly based upon clinical tradition and partly based on technological limitations of the design, such as requiring that each contact has a wire dedicated to conducting its signals to the recording apparatus. Studies on neocortical neuron density suggest that there are approximately 12 million neurons contained within the square centimeter of neocortex sampled by each one of these electrodes (See Pakkenberg B & Gundersen H J. Neocortical neuron number in humans: effect of sex and age. *J Comp Neurol* (1997) 384: pp. 312-320). It seems very unlikely that this would be a sufficient spatial sampling to capture even a small amount of the information available from this type of recording. The exact resolution for sensing and modulating activity in brain, peripheral nerve, spinal cord or other tissues in the body depends upon the particular application (e.g. brain-computer interface, functional electrical stimulation, alleviation of pain, etc.). A single electrode system that has the capability to resolve a broad range of these activities, tunable to a particular task, would be highly desirable and useful. In addition, being able to configure dimensions of the recording surface, through a broad range of configurations (e.g. to interface with a particular gyrus, dorsal root entry zone, peripheral or cranial nerve bundle) would be highly desirable, and contribute to great economy in power use, computational burden and minimize disruption of normal tissues.

In addition, the actual tissue contact region of the electrode system needs to be "changeable," as different applications may require recording from either the surface of tissues, from contacts that penetrate tissues to be close to particular types of cells, nuclei, nerve bundles or specific tissues, or perhaps from a combination or adjustable array of contact types. The proposed system is designed specifically with this type of flexibility in mind, allowing the "business end" of the system, the portion of the system that actually contacts biological tissues, to be adaptable and changeable in many different combinations.

To achieve the desired range of spatial sampling for signals of interest along with the desired area of coverage, it is clear that the number of sensor/effector contacts must be on the order of thousands, not tens or even hundreds, and that the spatial resolution of these sensor/effector contacts must be "scalable," (e.g. their effective size and spacing be adjustable without having to physically move or alter them). As an example, since each contact of existing brain/subdural electrode systems is either individually wired and assembled (e.g. Ad-Tech systems) or fabricated such that individual wires output signals from each contact (e.g. Utah array), it is clear that a more integrated design that incorporates multiplexing control techniques is needed to minimize the number of leads required and to make production feasible and cost effective. This also provides a safety advantage over current intracranial electrode systems, as there is evidence that the number of "tails" or leads extruding from the body can be related directly to morbidity in the case of subdural grids for brain recording, for example.

In the case of subdural electrodes for monitoring brain activity, other electrode designs have attempted to overcome the problem of spatial undersampling by making the electrodes smaller and more closely spaced. For example, the Utah Electrode Array 50 shown in FIG. 2 has an array of contacts spaced 0.4 mm apart. The Utah Electrode Array is described by Nordhausen C T, Maynard E M & Normann R A in "Single unit recording capabilities of a 100 microelectrode array," *Brain Res.* (1996), Vol. 726, pp. 129-140. While this provides a more desirable density of electrodes, the overall area of cortex that is sampled by the electrode array 50 is only 4 mm×4 mm, due to the small array size of 10×10 contacts. This amount of spatial coverage is insufficient for most clinical applications. Extending this electrode design to a larger array size is difficult because each electrode must be individually wired and because the array is made from inflexible silicon that does not conform to the shape of the tissues.

Several improvements have been suggested to fix the first problem of wiring complexity. Two such examples are illustrated in FIGS. 3 and 4. The example of FIG. 3 is described by Patterson W, Yoon-Kyu Song, Bull C, Ozden I, Deangellis A, Lay C, McKay J, Nurmikko A, Donoghue J & Connors B. in "A microelectrode/microelectronic hybrid device for brain implantable neuroprosthesis applications," *IEEE Transactions on Biomedical Engineering* (2004), Vol. 51, pp. 1845-1853, while the example of FIG. 4 is described by Aziz J, Genov R, Bardakjian B, Derchansky M & Carlen P. in "256-channel integrated neural interface and spatio-temporal signal processor, *Circuits and Systems,* 2006. ISCAS 2006. Proceedings. 2006 IEEE International Symposium on (2006), p. 4. In these electrode circuit designs, each electrode is connected to its own amplifier cell 60 (inset, FIG. 4). As shown in FIG. 4, each cell 60 includes a programmable high pass filter 61 and low pass filter 62, preamp 63, final amp 64, a sample-and-hold circuit 65, and an analog memory 66. In this way, each electrode can have its own dedicated amplifier and programmable filter bank. The outputs of all of the amplifier cells 60 in a given column are multiplexed together using an array of analog switches 70, and rows are multiplexed using an analog multiplexer 80 to allow all of the electrode outputs to be reduced to a single time-division multiplexed output line 85. This technique greatly reduces the number of wires that must exit the electrode array. However, the inflexible silicon substrate that these circuits are fabricated on still limits their use to sampling a small area of brain tissue where the surface can be approximately flat.

An ideal sensor/effector array would be flexible and stretchable to allow it to conform to the round and contoured surface (and within sulci and other recesses) of the brain or other biological tissues. Some attempts have been made to fabricate implantable electrodes using flexible printed circuit technology. For example, FIG. 5 illustrates the implantable electrodes 90 described in U.S. Pat. No. 6,024,702. However, this technique only allows for passive circuit elements, and so the problem of wiring complexity still remains.

The present invention addresses these and other needs in the art.

SUMMARY OF THE INVENTION

The present invention simultaneously overcomes the challenges remaining in the prior art by providing vastly increased sensor/effector density, increased area of coverage, and decreased wiring complexity through electrode multiplexing. By reducing the volume and complexity of intracranial wiring, and the volume of the implantable device, the proposed sensor array should also reduce morbidity and complications resulting from sensor implantation. Those skilled in the art will also readily appreciate that a sufficiently thin and flexible electrode array, such as that described, will allow for novel implantation techniques. These include, but are not limited to, endoscopic procedures and unfolding/unrolling sensor/effector arrays through a burr-hole, or introduced into blood vessels (e.g. on stents etc.) and other hollow structures via catheters. By enabling more minimally invasive procedures, the arrays of the invention can further reduce morbidity and mortality associated with sensor/effector implantation procedures. These same advantages exist for applications to other biological systems outside of the brain, such as heart, kidneys, stomach, cranial nerves, and other regions.

The microelectrode array of the present invention is fabricated using flexible and stretchable active electronics to overcome the difficulty in conforming to the surface of the brain and the geometry of other biological structures. Also, the array is designed in an extensible manner such that electrodes can be scaled up from micro to macro scale as needed, and such that the sensing elements can be interchanged with various light, electrical, chemical, temperature or other microfabricated sensing elements, as well as different kinds of electrical contacts, such as those that sit on the surface of (as oppose to penetrating) tissue.

The method and associated apparatus of the invention address the above-mentioned needs in the art by providing a high density sensor/effector array, such as a cortical surface electrode array, that is manufactured using flexible and stretchable active electronics so as to provide integrated multiplexed amplification and analog to digital conversion on the array; dynamic electrode reconfigurability by providing a grid of switches on the electrodes that switch based on number of contacts sampled, size of the electrodes, sampling rate, bit depth, shape and sampling region; coalescence of micro electrodes into macro electrodes; integrated patterned stimulation; wired or wireless real-time configuration and control; on-board closed-loop control; blood vessel imaging, and functional brain imaging (as electrical contacts could be changed for optical sensors) including locating the vessels and creating images; tracking of electrode position and migration; hardware and software tools for collecting, analyzing and displaying multi-channel, broadband neurophysiological or other biological signals; and providing digital data output using a high speed serial data bus.

An exemplary embodiment of the invention relates to an implantable cortical surface electrode array that incorporates active electronic and/or optical, chemical, or other sensor elements to greatly increase the number of electrodes that can be simultaneously recorded from and stimulated (including optical or chemical stimulation). The electrodes are arranged in a 2-dimensional grid in a first embodiment of the invention, but may be extended to a 3-dimensional grid, if penetrating electrode elements are used. The array is constructed on a flexible and stretchable substrate with incorporated active components that allow the effective size and number of contacts to be dynamically changed, as needed, through a wired or wireless means of communication. Active processing allows many channels to be combined either through analog or digital means such that the number of wires exiting the electrode array can be substantially reduced compared to the number of electrodes on the array. The individual electrodes are micro-scale and arranged in a high density array, but can be electrically connected through a series of analog switches to record as larger structures through active logic/control elements. Acquired signals are multiplexed down to a reduced set of wires or potentially converted from analog to digital signals directly on the electrode array.

In exemplary embodiments, the implantable cortical surface electrode array comprises a flexible substrate, an array of electrodes arranged on the substrate, and active electronic elements incorporated into the flexible substrate. The array of electrodes is ideally very small, whereby an array of at least 100×100 electrodes may be in an area no greater than 36 cm². The active elements selectively connect respective electrodes so as to enable the effective size, configuration and number of electrodes to be dynamically changed. The active electronic elements are flexible and/or stretchable, so as to better contact and conform to small changes in the brain surface (e.g. gyri, sulci, blood vessels, etc.) and include analog or digital switches between respective electrodes that are responsive to logic for selectively opening or closing to selectively connect the respective electrodes to each other. For example, a plurality of electrodes may be connected by the switches to form a macroelectrode.

The active electronic elements may also include an amplifier and an analog to digital converter for amplifying and digitizing signals detected by the electrodes. The active electronic elements may also be responsive to configuration and control signals provided by wire or wirelessly to the electrode array from a local or remote processing device. The processor may be part of the active electronic elements for a closed loop implantable embodiment and, in such case, may include algorithms that, for example, track the position of respective electrodes, identify migration of the electrodes on top of the cortical surface, and track electrode impedance and other measures of signal quality that can follow surrounding tissue reaction to the contacts (e.g. gliosis).

In an exemplary embodiment, the active electronic elements may comprise a buffer amplifier at each electrode and a set of multiplexing switches arranged in rows and columns. In such an embodiment, an analog to digital converter may be provided that receives and converts the outputs of all electrodes to a digital serial data stream.

BRIEF DESCRIPTION OF THE DRAWINGS

The foregoing summary, as well as the following detailed description of the embodiments of the present invention, will be better understood when read in conjunction with the appended drawings. For the purpose of illustrating the invention, there are shown in the drawings embodiments which are presently preferred. As should be understood, however, the invention is not limited to the precise arrangements and instrumentalities shown. In the drawings.

DETAILED DESCRIPTION OF EXEMPLARY EMBODIMENTS

Figure 1:
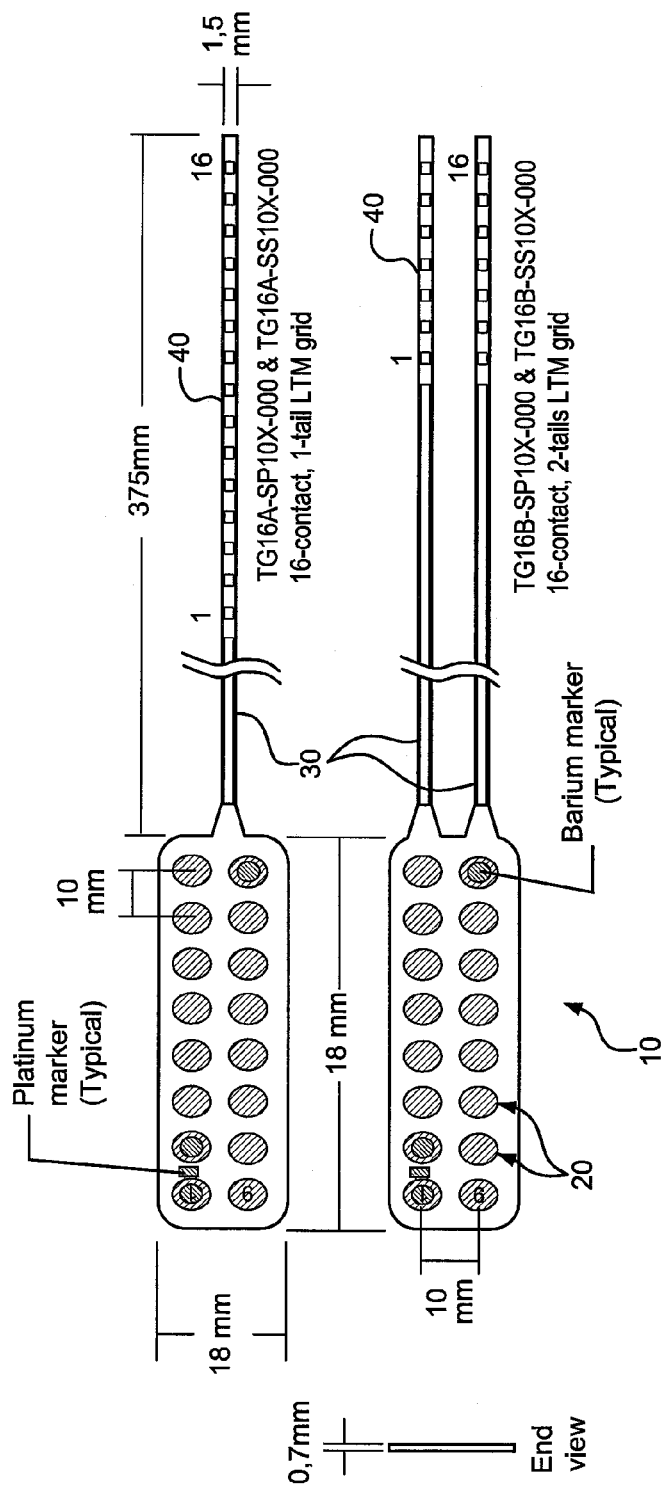
FIG. 1 illustrates a prior art flexible subdural grid electrode that is capable of sampling over a large surface area, but has poor spatial resolution due to the large 10 mm spacing between electrodes.
Figure 2:
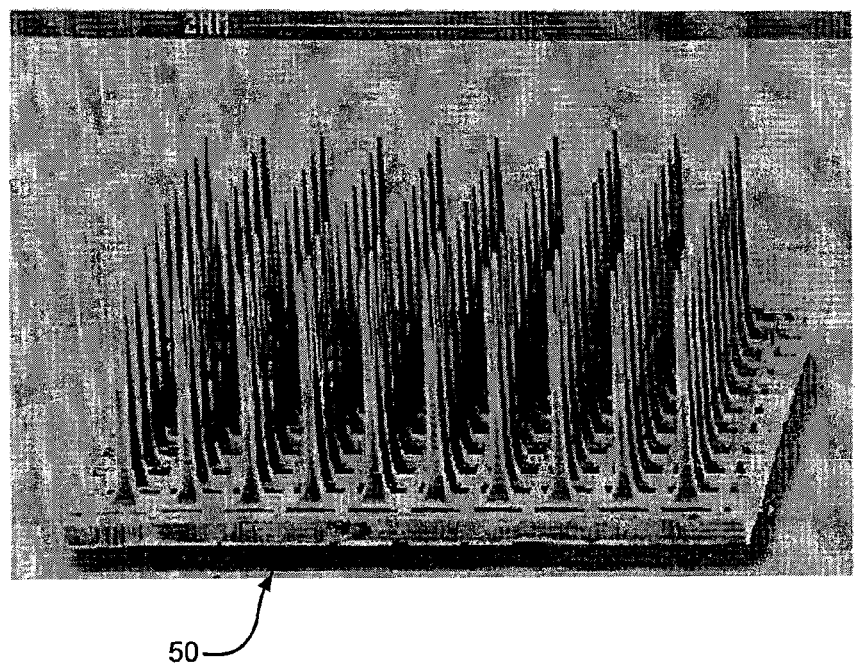
FIG. 2 illustrates a prior art microelectrode system having contacts spaced 400 μm apart, but is only capable of sampling a very small area of approximately 4 mm×4 mm.
Figure 3:
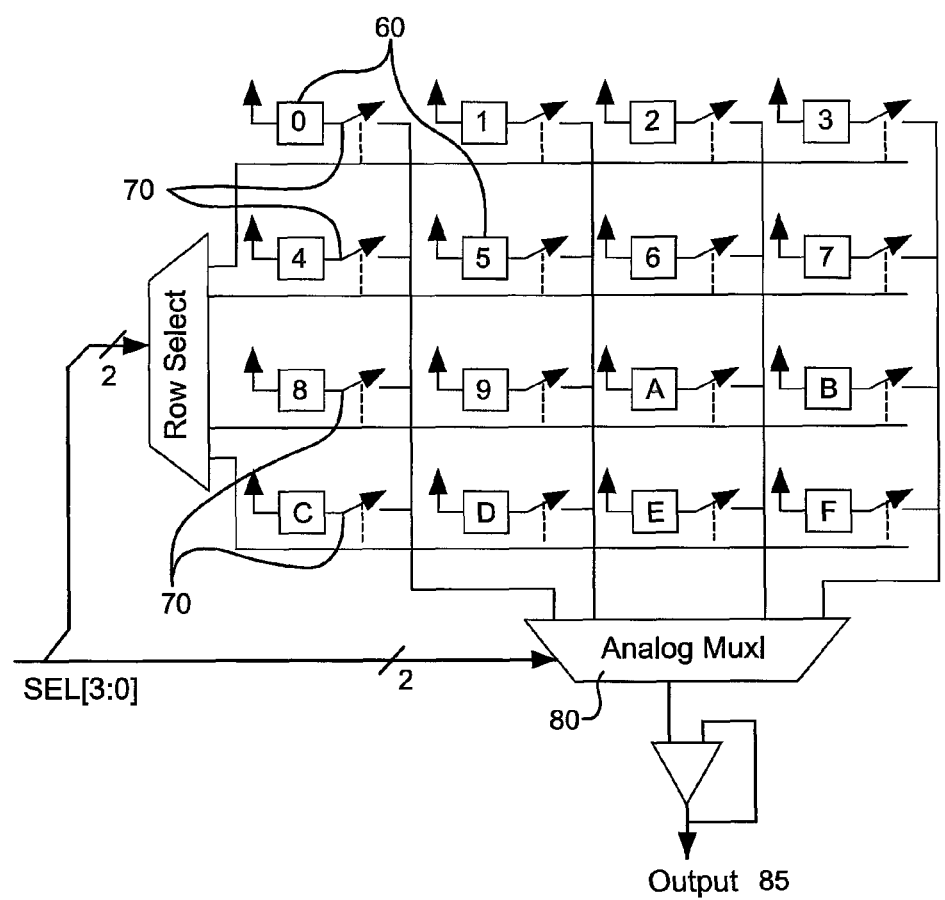
FIG. 3 illustrates a prior art multiplexed analog electrode system for inflexible microelectrode arrays.
Figure 4:
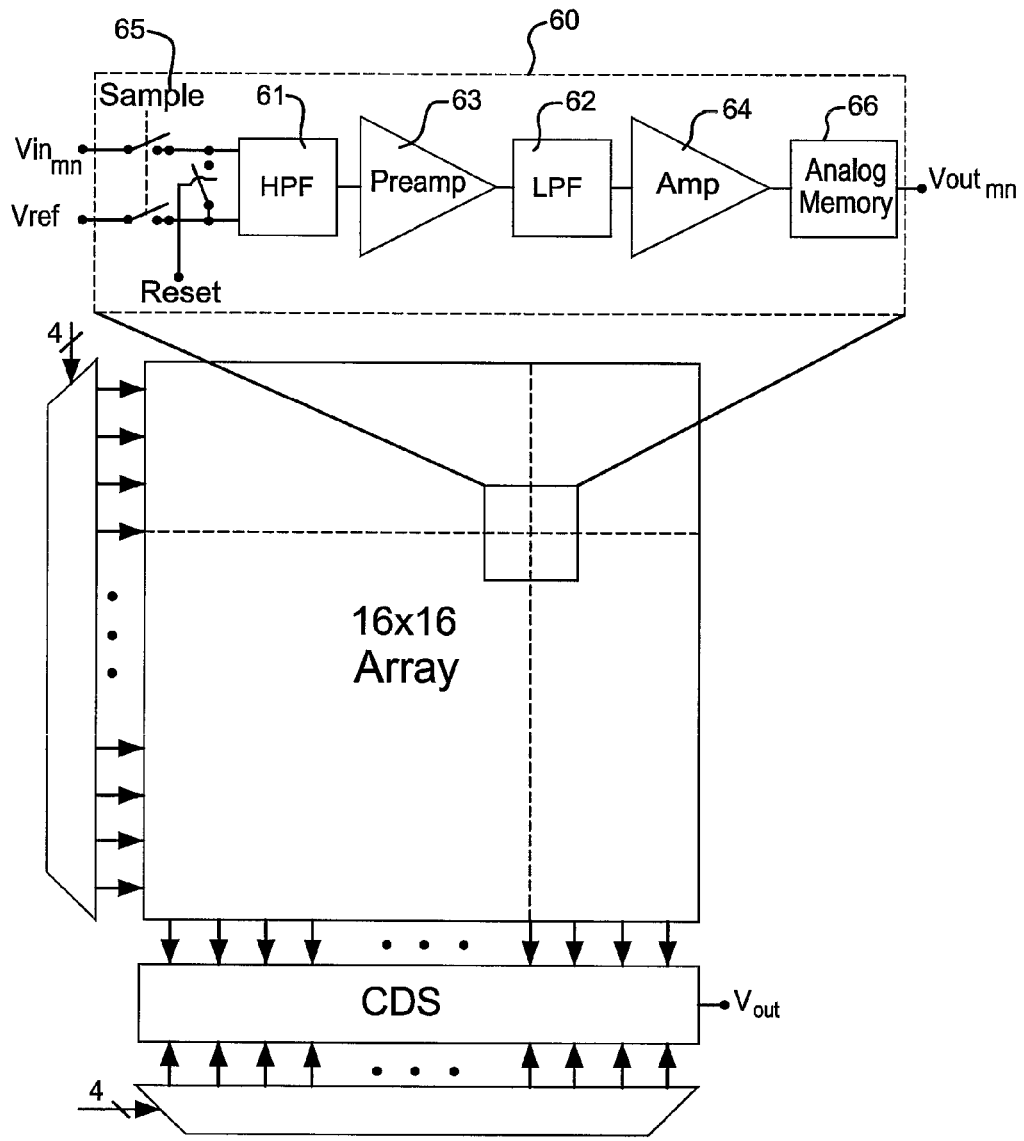
FIG. 4 illustrates another prior art multiplexed analog electrode system for inflexible microelectrode arrays.
Figure 5:
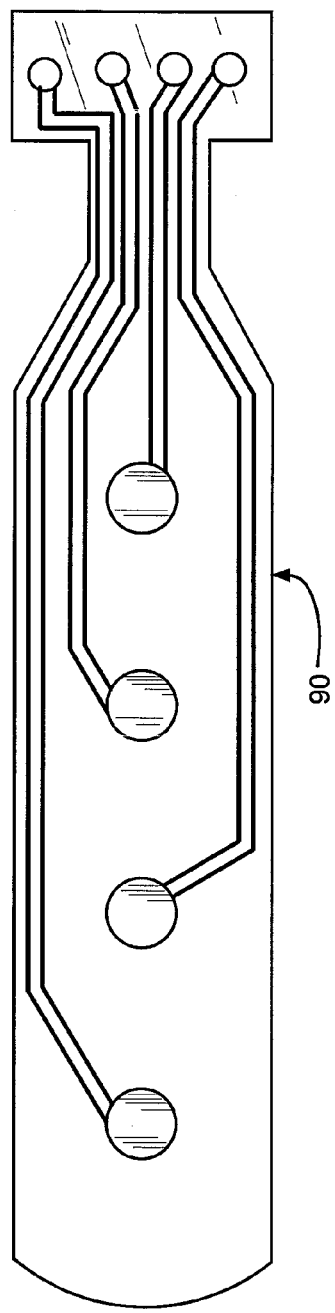
FIG. 5 illustrates a prior art flexible printed circuit electrode array that suffers from the limitation of wiring complexity.

A detailed description of illustrative embodiments of the present invention will now be described with reference to FIGS. 1-17. Although this description provides a detailed example of possible implementations of the present invention, it should be noted that these details are intended to be exemplary and in no way delimit the scope of the invention.

The following definitions will be used throughout this specification:

Sensor: Any element that can be used to transduce a biological signal into an electrical or other signal. Examples of sensors include: electrical contacts for recording electrophysiological signals, optical detectors for recording light correlates of biological activity, chemical sensors for detecting changes in chemical concentrations or PH (e.g., chloride, neurotransmitters, lactate, glucose, other metabolites, neuroactive compounds, medications, biological substances such as tumor-secreted factors, etc.), devices for measuring temperature, force, acceleration, movement, pressure, etc.

Effector: Any device that takes a signal and introduces an intervention to modulate biological (e.g., brain) activity. Examples of effectors include electrical stimulators, photo/light-emitters (e.g., for activating brain tissues impregnated with a light responsive compound), chemical releasing/infusion devices, devices that change temperature, pressure, and/or acceleration, and devices that introduce electrical, magnetic or other fields, etc. Illumination sources such as a light source or other source that can activate tissue for diagnostic or monitoring purposes may also be used. For example, such illumination sources may be used to activate brain tissue to interrogate its function but not necessarily to modulate its activity.

In the following specification, the term "sensor" will be understood to also include functionality of the effector as defined above.

While exemplary embodiments of the invention are described herein in the context of a system of intracranial electrodes to record from and stimulate the brain, those skilled in the art will appreciate that the invention may also be used as a configurable sensor and/or effector in the following types of biological systems. The following list is not meant to be exhaustive, but rather representative of the broad array of monitoring and modulation functions that can be subsumed by the invention:

Cardiac sensors/effectors, such as for cardiac electrophysiology testing, and devices such as pacemakers, defibrillators, electrically active catheters for going inside the heart and blood vessels, and the like;

Neuroprostheses for special sensory organs, e.g. artificial retinas, cochlear implants, balance (vestibular and other cranial nerve interfaces) prostheses, devices to aid in taste, smell, physical sensation, proprioception, and other similar functions;

Neuroprostheses for recording and functional electrical stimulation of motor and other central and peripheral nerves for afferent and efferent functions (e.g. motor and sensation);

Implanted devices to go into tissues, such as intravascular and other forms of sensor/effector covered stents for deployment in the brain or blood vessels;

Implantable devices for organ function monitoring, or monitoring of tissues for the presence or recurrence of tumors, cancer, metastases, etc.;

Implantable sheets of electrodes that can be wrapped around structures for patterned recording, stimulation or other functions, for example, pacing stomach or intestinal contractions to restore mobility to paralyzed tissues (e.g. due to diabetic gastroparesis); and Endoscopic introduction into other cavities in the body, for example, in and around the heart, abdomen, inside organs, on muscular structures such as the bladder neck, inside blood vessels, on stents, etc.

Electrode Multiplexing

At the outset, the inventors recognize that to sample hundreds or thousands of electrodes simultaneously, a multiplexing strategy is desired to reduce the number of wires that must come off of the electrode array. Reducing the number of wires coming off of the array is also advantageous because the number and size of leads implanted along with an electrode array has been found to correlate with risk of infection, brain swelling, and complications from implantation surgery. In addition, having electrode arrays with hundreds of connections greatly increases the probability of operator error in making the connections and properly setting up the labels on each channel.

Electrode array embodiments that embody exemplary multiplexing embodiments will be described in the following section.

Individually Buffered and Multiplexed Inputs

Figure 6:
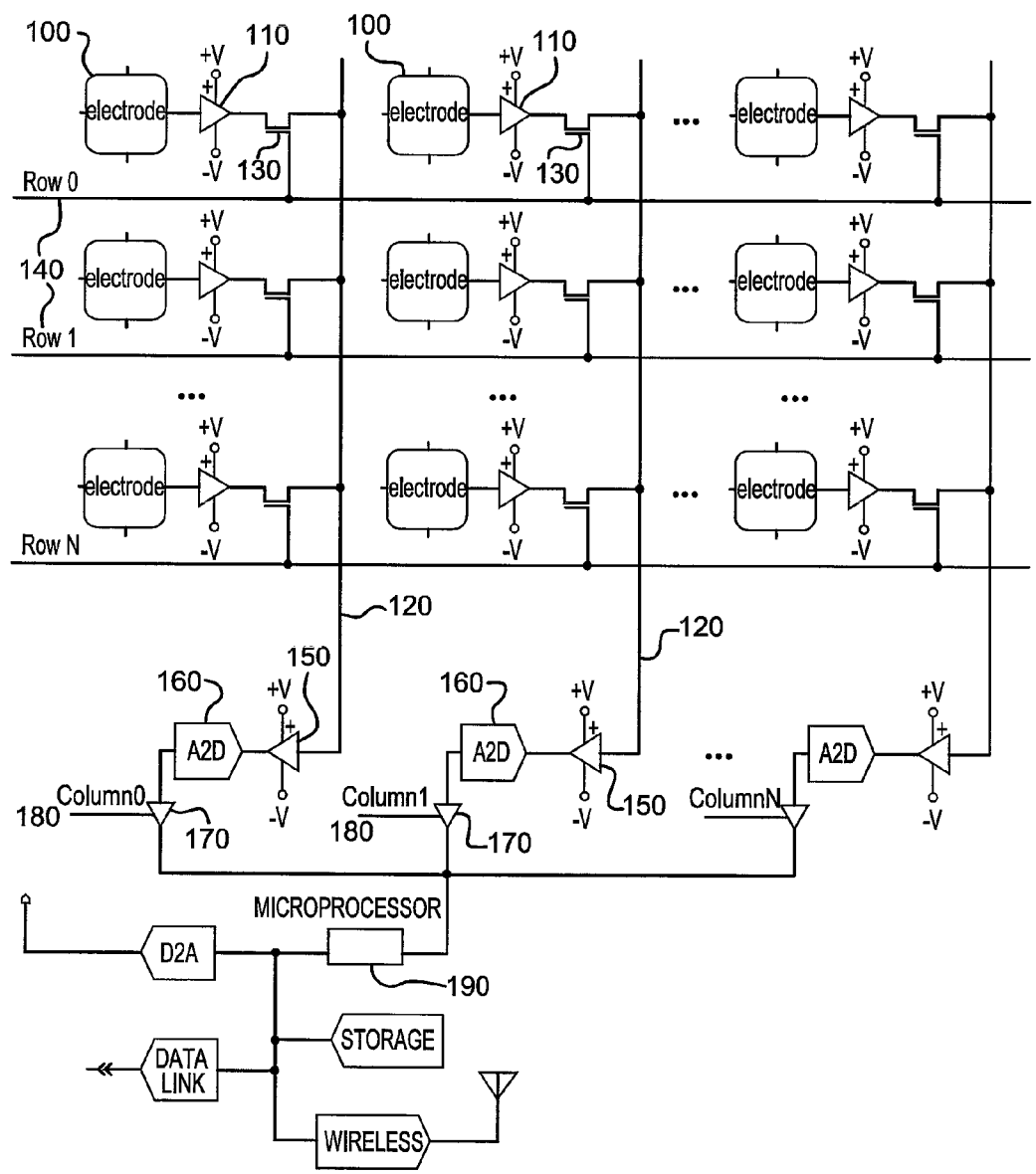
FIG. 6 illustrates an exemplary embodiment of the invention incorporating a digital signal processor and the capability for microstimulation that may be used in a closed-loop clinical device for recording cerebral activity and stimulating for diagnostic or therapeutic purposes.

In an exemplary embodiment of the present invention, individual buffer amplifiers are incorporated at each electrode and their outputs are multiplexed together. This design is illustrated in FIG. 6. Each electrode contact 100 is directly attached to a dedicated preamplifier 110 that provides some gain to the signal and a low-output impedance to drive the column line 120. The output of the preamplifier 110 is connected to the column line 120 through an analog switch 130.

Figure 7:
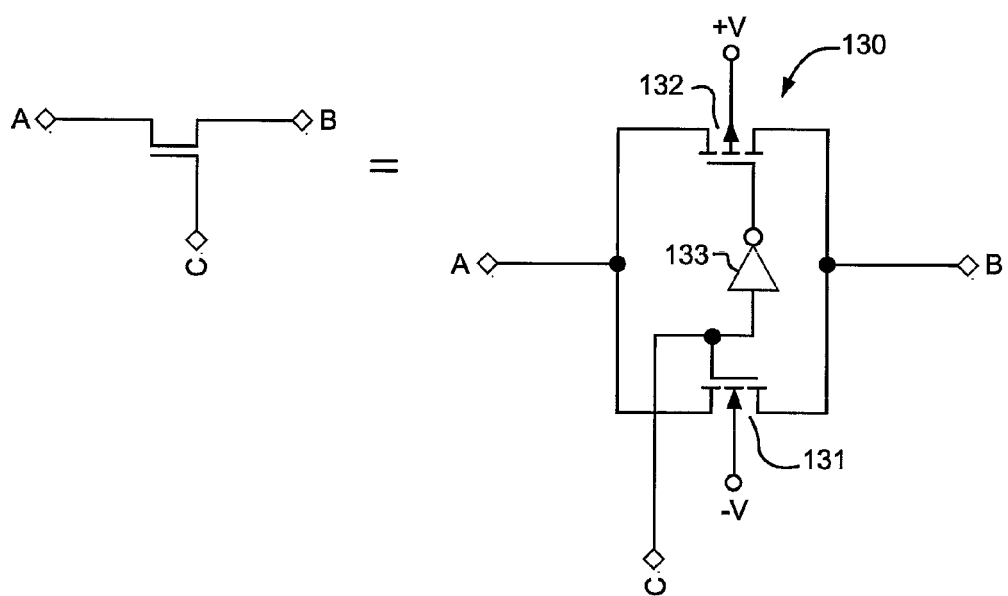
FIG. 7 illustrates an exemplary embodiment of the analog switches utilized in FIG. 6.

The circuit details of the analog switch are shown in FIG. 7. The NMOS pass transistor 131 is driven by a digital logic signal, C, while the PMOS pass transistor 132 is driven by the output of the inverter 133. In this way, both pass transistors are active (conducting) when C is at a high logic level and both pass transistors are inactive (non-conducting) when C is at a low logic level. This allows analog signals to either pass through the device or not based on a digital logic control signal, C. Alternatively, FIG. 12 illustrates one possible embodiment of the analog switches utilized in FIG. 11 where the analog switch 130 is coupled to a static RAM cell 134 to maintain the switch state (open or closed) without intervention by the system logic.

FIG. 6 shows columns of N electrodes 100, preamplifiers 110 and analog switches 130. By activating a specific row signal 140 and de-activating the other N−1 row signals, the output of the selected row amplifier will be allowed to drive the column line 120. In this manner, any one of the N rows can be selected to drive the column amplifier 150. This column amplifier 150 provides additional gain to match the range of the signal to the input range of the column analog to digital converter 160. The column analog to digital converter 160 converts the analog signals from the electrode channels to digital values. The digital output of the column analog to digital converter 160 is connected to a digital buffer 170, and the outputs of all N digital buffers 170 (one for each column) are connected together. Each column signal 120 can be individually selected via the N column select signals 180. In this way, the data from the N column analog to digital converters 160 can be combined down to one digital input on the integrated microprocessor 190.

Figure 8:
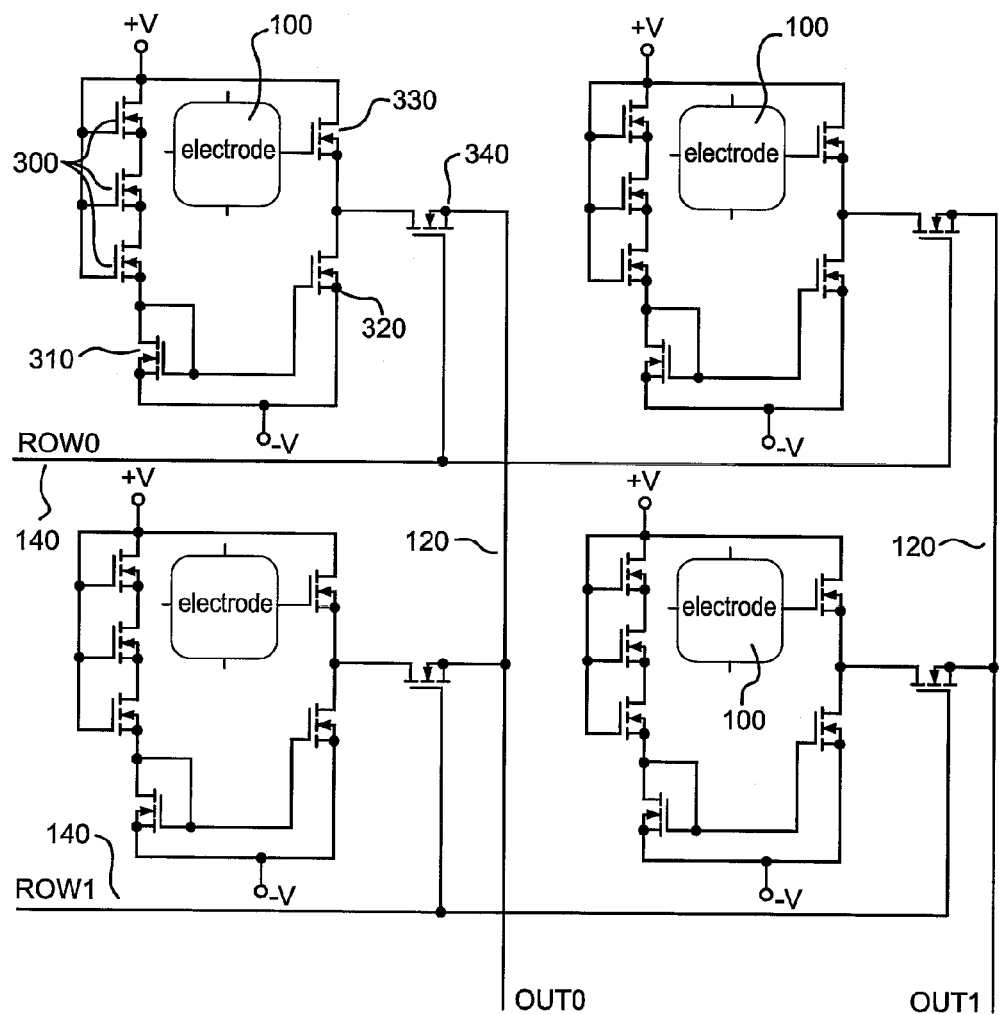
FIG. 8 illustrates an exemplary embodiment of the circuit shown in FIG. 6.

FIG. 8 illustrates one possible embodiment of the circuit shown in FIG. 6. The circuit has been simplified to only show the amplifiers and analog switches for 4 electrodes, arranged in a small grid of 2×2. However, FIG. 6 illustrates how this basic design can be extended to any number of rows and columns. In FIG. 8, the amplifier has been implemented using a source-follower architecture. In this configuration, three NMOS transistors 300 have been connected as a current source. Two additional NMOS transistors 310 and 320 are configured as a current mirror and a final NMOS transistor 330 forms the active load. These six transistors comprise the amplifier (110 in FIG. 6). The output of this amplifier is connected to a multiplexing transistor 340 (130 in FIG. 6) which serves to selectively enable the output of that amplifier.

Modified CMOS Image Sensor Structure

Figure 9:
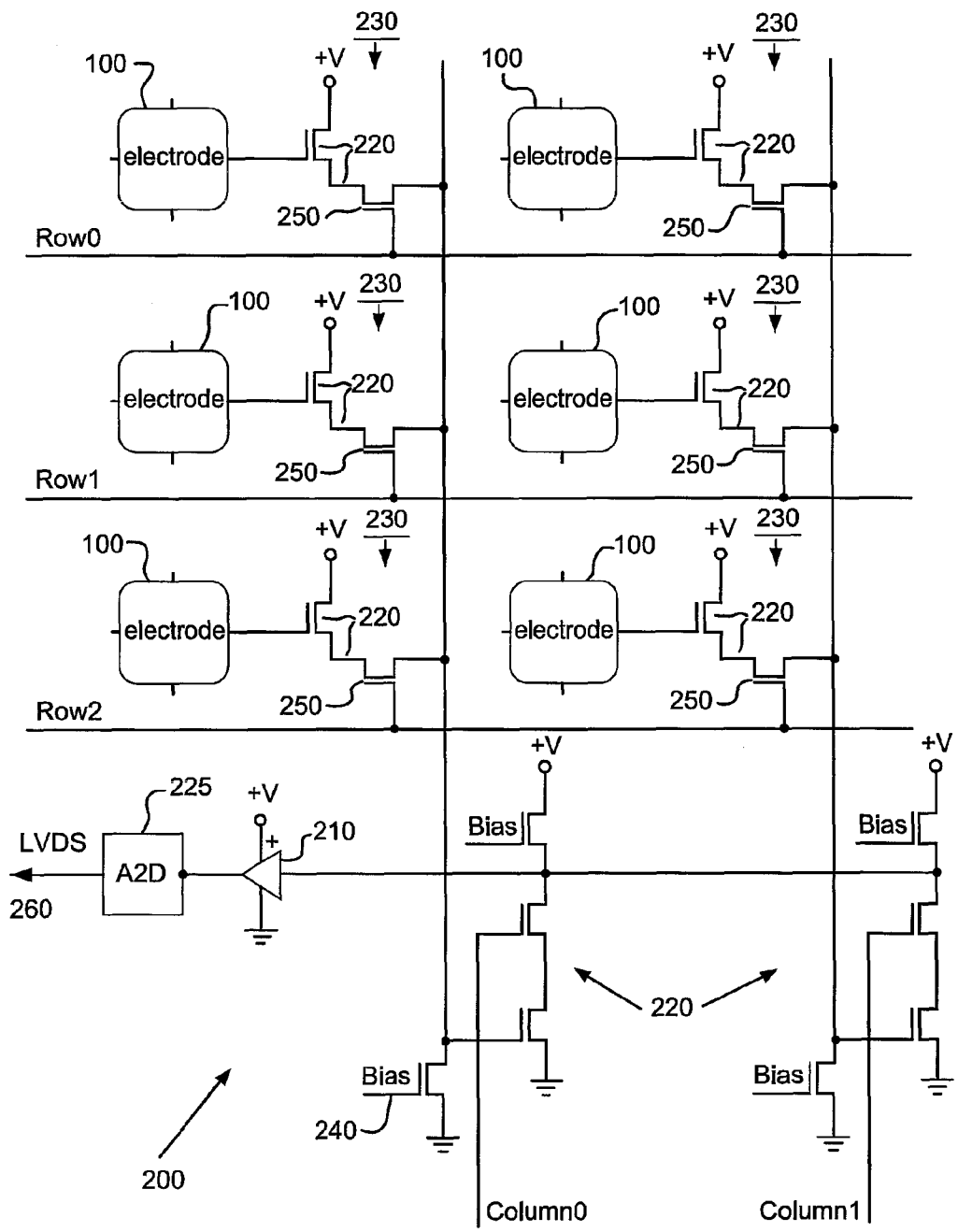
FIG. 9 illustrates an alternate electrode multiplexing technology based on a CMOS digital imaging circuit.

In an alternate embodiment of the invention, a CMOS digital image sensor has been modified to multiplex the electrodes 100. As illustrated in FIG. 9, such a modified CMOS image sensor 200 includes an array of electrodes 100 that are connected to output amplifier 210 and addressed by suitable addressing circuitry 250. In an exemplary embodiment, an analog to digital converter 225 may be connected to the output of output amplifier 210 so as to provide A/D conversion on the image sensor array 200. Correlated double sampling may be removed to prevent inadvertent stimulation of the cortex during the reset operation. Further modifications may be required to reduce the noise floor of the image sensor array 200.

The CMOS image sensor of FIG. 9 works as follows. Each microelectrode 100 is connected to the gate of a field effect transistor 220 of amplifier 230. This transistor 220 is connected to the common vertical bias transistor 240 by means of a horizontal row select transistor 250. In this way, one half of an amplifier is formed at each pixel and the other half is shared among all the pixels in a given column. Another similar configuration allows a given column to be selected to drive the output amplifier 210. This high bandwidth amplifier 210 provides the gain required to match the detected EEG signals to the range of the analog to digital converter 225 that samples the signal and outputs the digital data over a single Low-Voltage Differential Signaling (LVDS) high speed serial data bus 260. For example, a commercially available 10-bit, 20 MSPS analog-to-digital converter 225 may be used that operates using less than 50 mW so that it may be integrated onto the electrode array 200 to provide an output bit stream for recording and storage.

Modified CCD Structure

In another alternate embodiment, a CCD, or Charge Coupled Device, is modified in its design to accept direct electrical input, instead of light input. In this modality, the EEG signal creates packets of charge in the device that are transferred along the device, until ultimately read out.

Electrode Details

The flexible electrode arrays described above and illustrated in FIGS. 6 and 9 include $N^2$ electrodes. These electrodes can be many possible types of electrodes. For example, the electrodes 100 may be made of gold, platinum, platinum-iridium, tungsten or other substances including conductive non-metals. The electrodes 100 may be in the shape of "bumps", flat round or square patches, or small penetrating spikes. Other embodiments of the "tissue end" of this electrode system may penetrate tissue (e.g. brain) using tetrodes, silicon and platinum microelectrode arrays and silicon microprobes, among others.

Figure 10:
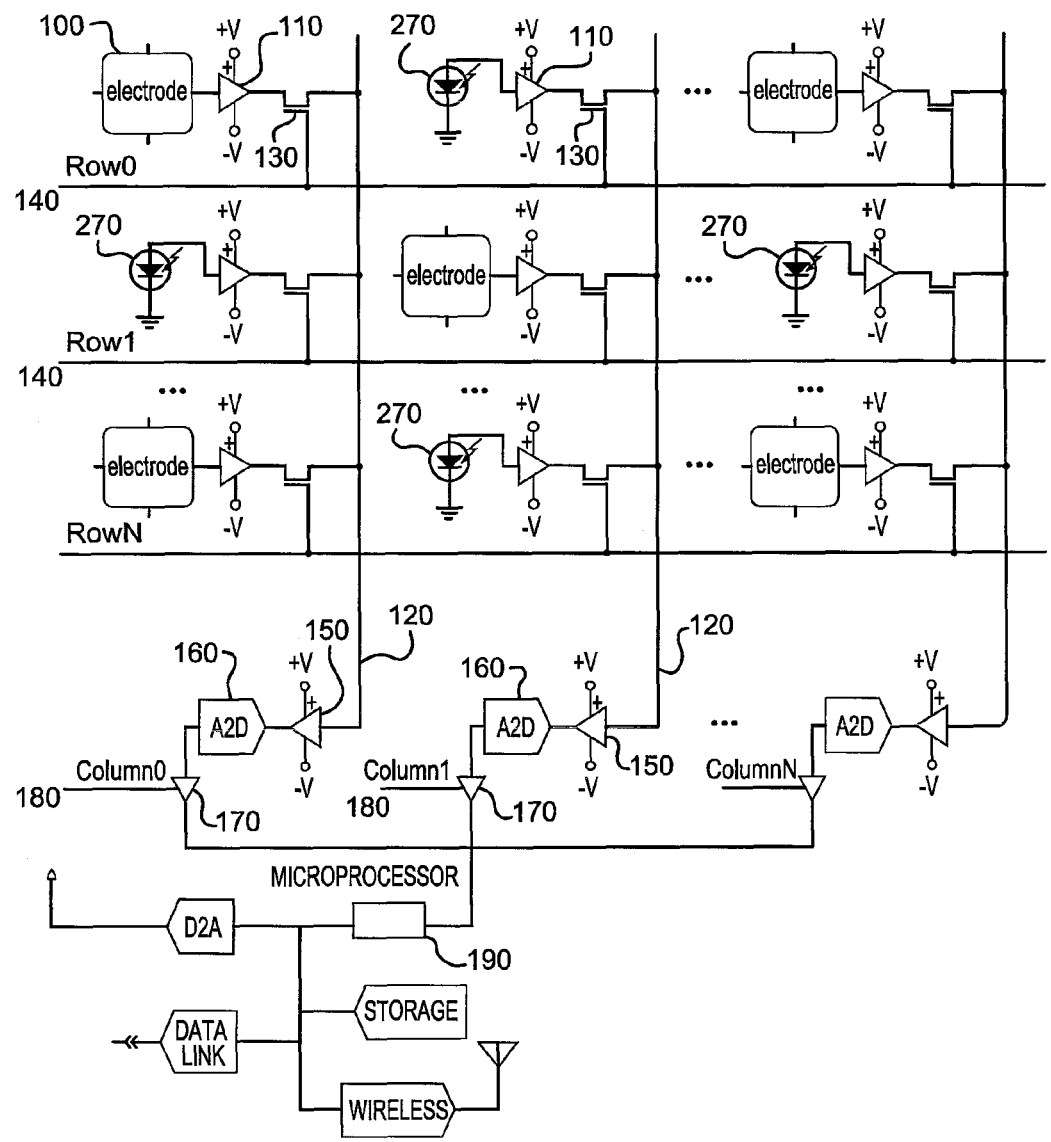
FIG. 10 illustrates how different types of sensors (e.g., optical detectors, or chemical, temperature, pressure or other measurement devices) can be designed into the array of FIG. 6 in place of some or all of the electrodes.

Additionally, the electrodes 100 do not need to be electrodes at all. Some or all of the electrodes 100 may be replaced with other solid-state sensors that can be designed to output an electrical signal. For example, FIG. 10 shows a variation of the circuit of FIG. 6 where some of the electrodes 100 have been replaced by photodiodes 270. With an appropriate illumination source, these light sensors 270 could be used to measure local blood oxygen concentration, blood flow, or other parameters. Other solid-state sensors that could be integrated onto the array in place of one or more electrodes to measure local chemical concentrations, pH, temperature, force, magnetic field and more.

Electrode Coalescence

Figure 11:
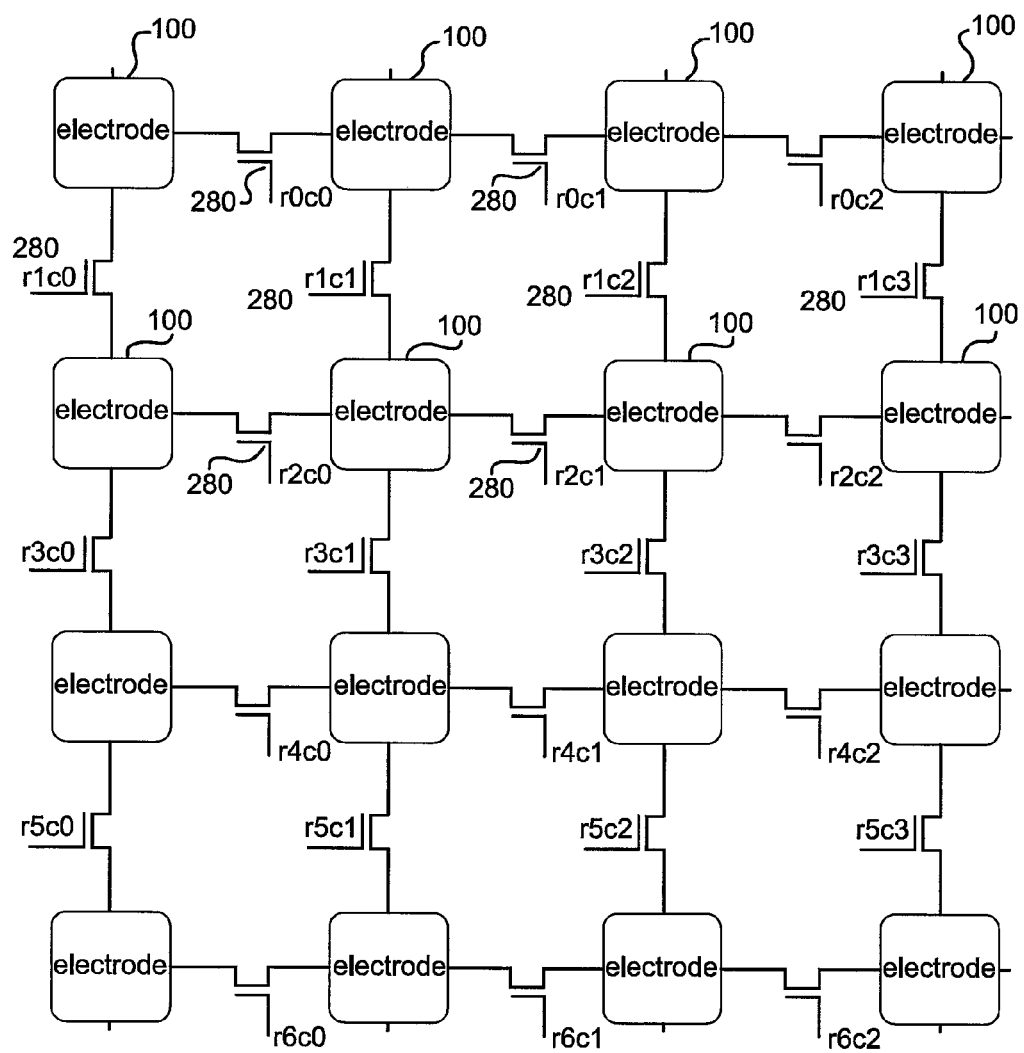
FIG. 11 illustrates how adjacent electrodes in a micro electrode array are interconnected by a series of analog switches, different from those in FIG. 7, to allow the effective size and spacing of the electrodes to be adjusted on the fly.
Figure 12:
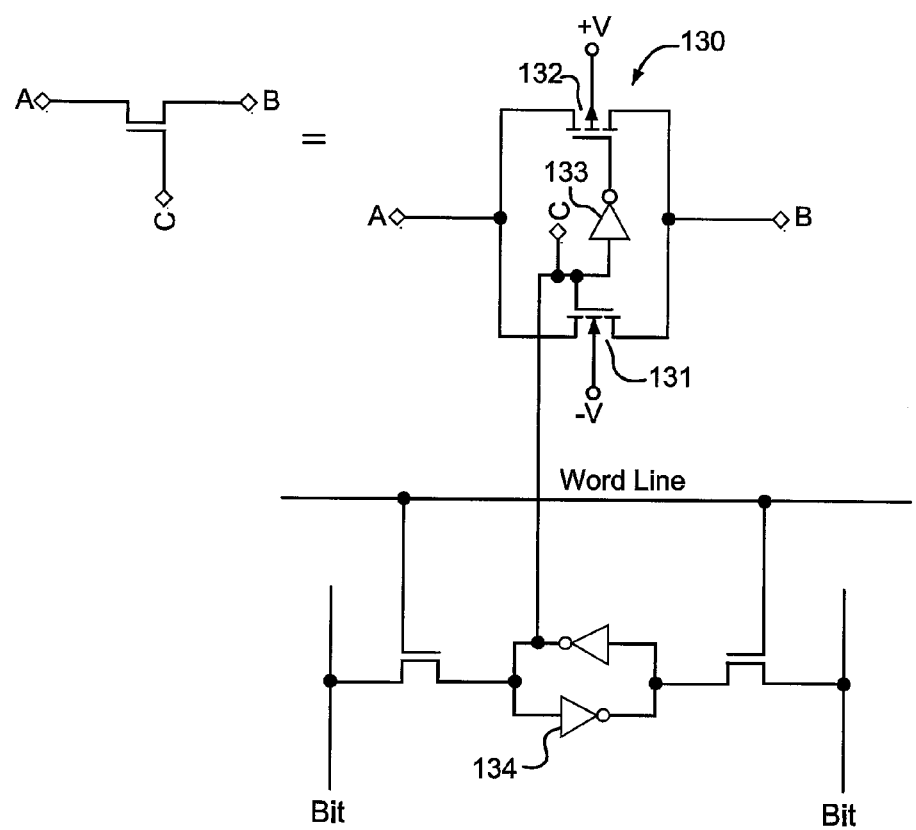
FIG. 12 illustrates one possible embodiment of the analog switches utilized in FIG. 11 where the analog switch is coupled to a static RAM cell to maintain the switch state (open or closed) without intervention by the system logic.
Figure 13:
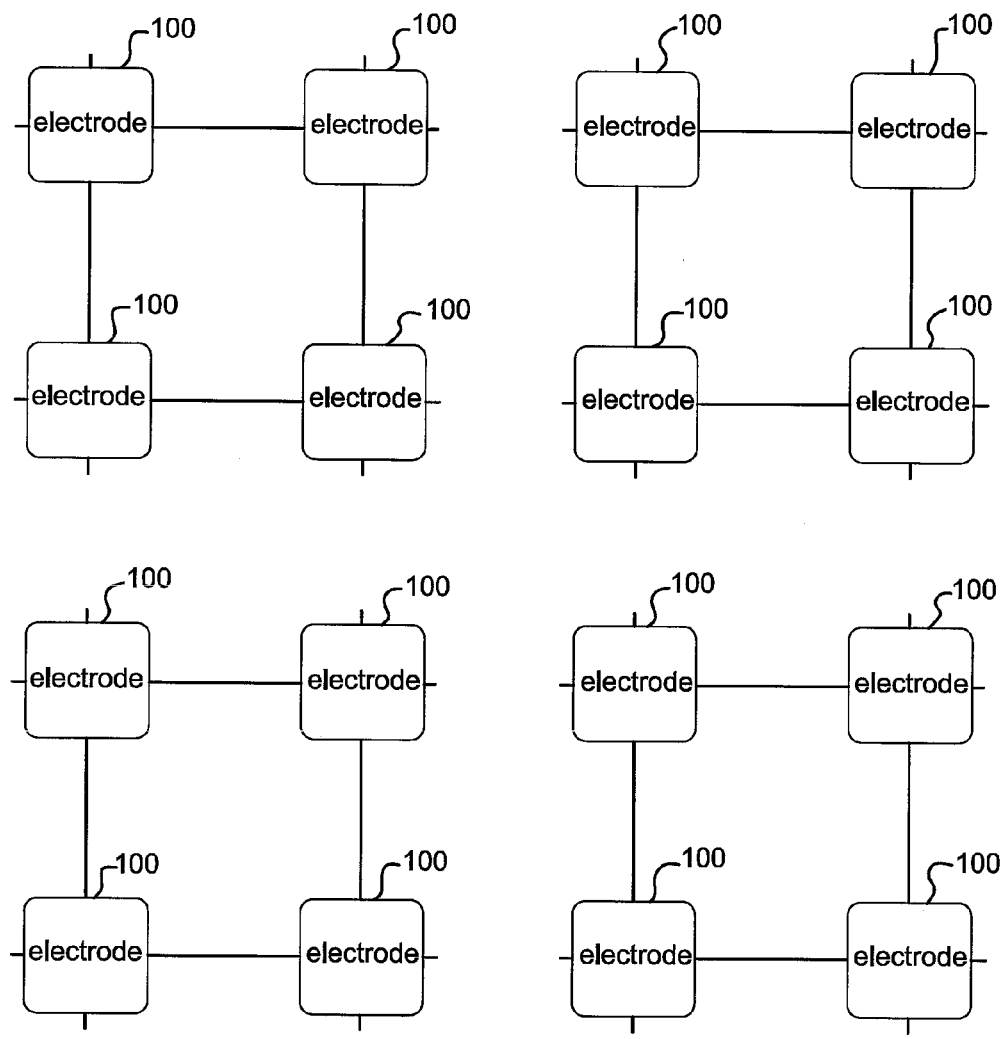
FIG. 13 illustrates the resulting effective circuit when 4×4 groups of electrodes are combined by selectively closing the multiplexing analog switches in the array.

The analog switch 280 of FIG. 11 placed between adjacent micro-electrodes 100 allows the creation of electrically connected contacts of arbitrary size. For example, if the following switches in the example schematic are programmed as follows:

| Active | Inactive |
| --- | --- |
| r0c0, r0c2 | r0c1 |
| r1c0, r1c1, r1c2, r1c3 | r2c1 |
| r2c0, r2c2 | r3c0, r3c1, r3c2, r3c3 |
| r5c0, r5c1, r5c2, r5c3 | r4c1 |
| r6c0, r6c2 | r6c1 | then the resulting effective circuit will be the circuit shown in FIG. 13. The net result of this transformation is a 4× reduction in spatial sampling. This would allow a 4× increase in sampling rate or bit depth or a similar reduction in power consumption. Further spatial aggregation would be possible as well, right up to or beyond the size of current macro electrodes. A dynamic algorithm could be employed that would intelligently combine and dissociate electrodes such that areas of interest could be automatically identified and spatially sampled at a higher density while areas of less interest could be sampled at a lower density. Furthermore, the sampling sites could be customized such that areas that do not need to be sampled, like vasculature, could be ignored. This might be done, for example, by taking a digital picture of the area to be recorded, or abstracting this from an MRI image, and then programming the electrode array to record only from those electrodes in contact with regions of interest, or to silence contacts positioned over electrically inactive regions. It is important to note that being able to customize sensor/stimulator size by aggregating a number of electrodes, may have distinct neurophysiological advantages based upon features of the cortical or subcortical structure or network being recorded or stimulated. For example, if a group of contiguous cortical columns of a particular dimension is the basic functional unit that needs to be monitored or stimulated, this structure might best be recorded or stimulated with electrodes aggregated into groups of 4 or 16, rather than single contacts. Similarly, if a single cortical column need be activated, this might be best done with single contacts, or aggregated contacts from a system in which the electrodes are more closely spaced.

Stimulation

An additional overlay of demultiplexing logic plus a digital to analog converter (160 of FIG. 6) can be added to the electrode array to allow micro-stimulation at one or more contact sites. The intelligence may also be provided in an interface or a remote processing unit, as desired. The stimulation for the electrodes may be pre-programmed patterns developed to accomplish particular tasks, such as to modulate epileptiform activity, initiate or inhibit function, map blood vessels, and map functions of neural tissue. In other applications, stimulation might be controlled in closed loop, via active software, based upon recorded signals or using continuous feedback to modulate neuronal activity for therapeutic purposes.

On-Board Closed Loop Control

An additional microprocessor or digital signal processor 190 can be added to the electrode array of FIG. 6 to enable its use as a stand-alone closed-loop control system. This system would incorporate a sampling control system, signal processing, and a stimulation control into the microprocessor or digital signal processor 190 to allow the electrode array to become a fully self-sufficient implantable device. The processor 190 may include algorithms to provide for vessel or functional brain imaging, location and recording, and to track the position of respective electrodes and identify migration of the electrodes 100 within cortical tissue. In order to conserve battery life, the number of channels sampled can be reduced to only the channels that are of most interest and clinical value. The other amplifiers on the array can be shut down or only sampled periodically to reduce power consumption and data processing requirements. This embodiment also allows for periodic updating of the electrodes used as networks evolve and function changes or migrates over time. Of course, hardware and software tools may be implemented in conjunction with the electrode arrays described herein to collect, analyze, and display the multi-channel, broadband neurophysiological signals detected by the electrode arrays of the invention.

Area

A conventional neural amplifier occupies 0.16 mm$^2$ of space using a very conservative 1.5 um-CMOS process (Harrison R & Charles C., "A low-power low-noise CMOS amplifier for neural recording applications," *IEEE Journal of Solid-State Circuits*, (2003) Vol. 38, pp. 958-965). To achieve a 100×100 array in 36 cm$^2$, each amplifier must occupy less than 0.36 mm$^2$ of space. This means that using a similar design would leave >55% of the surface area available for interconnects and other logic, which should make the design feasible.

Data Storage and Archiving

A 100×100 grid array will contain 10,000 electrodes. Sampling each electrode at 2000 Hz will yield a total sampling rate of 20 MSPS. At 12 bits/sample, this yields 30 MB/s of data. This becomes 101 GB/hr and 2.4 TB/day. However, a simple differential encoding scheme should be able to reduce this data set by at least a factor of 4. Considering that 1 TB single hard drives are currently available and that hard drive prices continue to fall, this amount of data seems large but manageable. If needed, the data can be down-sampled and the recording can be adjusted to the task as required. For example, the patient could be recorded at a sampling rate of 500 Hz per channel at rest and automatically adjusted to 2 KHz per channel synchronized with particular cognitive tasks or periods of increased probability of seizure onset. Another strategy would be to collect data at the best quality all the time and then utilize a background server task that compresses, prunes and archives data to be saved.

Interface

Once the data is converted from analog to digital, the samples need to be transmitted to a computer for storage and analysis. This link needs to use as few wires as possible, while consuming little power and providing a reasonable cable length, interference tolerance and room to expand to larger array sizes. The use of an LVDS link (260 of FIG. 9) reduces the power consumption of the data transmission, reduces radiated electromagnetic noise and allows data transmission of up to 1 Gigabit per second and beyond over a single pair of wires. At the current estimated data rate of 240 Mbps, several transmission techniques should be capable of performing this task. Among them are USB 2.0, Firewire 400/800, eSATA and Gigabit Ethernet. As an example, a USB 2.0 interface chipset with integrated microprocessor (See Ez-usb fx21p™ usb microcontroller at http://download.cypress.com.edgesu-ite.net/design_resources/datasheets/contents/ cy7c68013a_8.pdf) consumes 165 mW of power while delivering up to 53 MB/s data transfer rate. This should be sufficient for integration into a device. If further power savings are required, a custom low-voltage differential signaling (LVDS) protocol can be designed that can attempt to better meet the needs presented by this electrode array.

Power

A calculation of the maximum allowable power consumption can be estimated from the simulations presented by Ibrahim T S, Abraham D & Rennaker R L in "Electromagnetic power absorption and temperature changes due to brain machine interface operation," *Ann Biomed Eng.*, (2007) Vol. 35: pp. 825-834. The study concludes that 78 mW/cm$^2$ is an allowable power dissipation for a 1 degree Celsius temperature rise. Another work states that a heat flux of only 80 mW/cm$^2$ can cause tissue damage (T M, Harasaki H, Saidel G M & Davies C R, "Characterization of tissue morphology, angiogenesis, and temperature in the adaptive response of muscle tissue to chronic heating," *Lab Invest.* (1998), Vol. 78, pp. 1553-1562).

A current design low-power amplifier for neural recordings consumes 15 µW per channel (Aziz J, Karakiewicz R, Genov R, Chiu A, Bardakjian B, Derchansky M & Carlen P., "In vitro epileptic seizure prediction microsystem," *Circuits and Systems*, 2007, *ISCAS* 2007. *IEEE International Symposium on* (2007), pp. 3115-3118). This means that a 10,000 channel electrode array might consume 150 mW of power. If these 10,000 channels are spread out over a 36 cm$^2$ electrode array, the threshold for damage might be as high as 2.88 W. Therefore, 150 mW may be an acceptable level of power consumption. To improve the safety of the device, solid state temperature sensors could easily be integrated into the array to measure thermal rise. If an unsafe temperature rise is measured, the array sampling rate can be turned down to reduce power. If this fails to control the temperature rise, the array can be completely turned off.

Additionally, the power consumed by all the active elements on the array should be considered as well. If the power consumed by the amplifiers, analog to digital converter(s), microprocessor and interface logic (Table 1) is added up, then the total power consumption of the array can be estimated to be around 430 mW. This level of power consumption and associated heat generation may be acceptable for implantation but test data is required for safety evaluations of different tissues.

TABLE 1

Power budget breakdown

| Component | Power |
|---|---|
| 10,000 amplifiers | 150 mW |
| Analog to digital conversion | 65 mW |
| Misc logic power | 50 mW |
| Microprocessor and USB Interface | 165 mW |
| Total | 650 mW |
| Max Allowable power in 36 cm$^2$ | 2880 mW |

The active elements on the array also may be powered by power induced from sources outside of the body such as through inductive coupling from RF coils, and the like, to permit remote activation, data transmission, etc. when needed or desired from the active elements, without requiring an integrated power source.

Fabrication Techniques

The electrode array of the invention may be manufactured using one of a number of available fabrication techniques. For example, in accordance with a first technique disclosed by J. Rogers at the University of Illinois at Urbana-Champaign, buckled silicon nanoribbons have been shown to provide a stretchable form of single-crystal silicon for high-performance electronics on rubber substrates (FIG. 14) (See Kyang et al. in "A Stretchable Form of Single-Crystal Silicon for High-Performance Electronics on Rubber Substrates," *Science*, Vol. 311, 13 Jan. 2006). J. Rogers has also shown that printed semiconductor nanomaterials may be used to form heterogeneous three-dimensional electronics (See Choi W M, Song J, Khang D, Jiang H, Huang Y Y & Rogers J A, "Biaxially stretchable 'wavy' silicon nanomembranes," *Nano Lett.*, (2007) Vol. 7, pp. 1655-1663).

Figure 14:
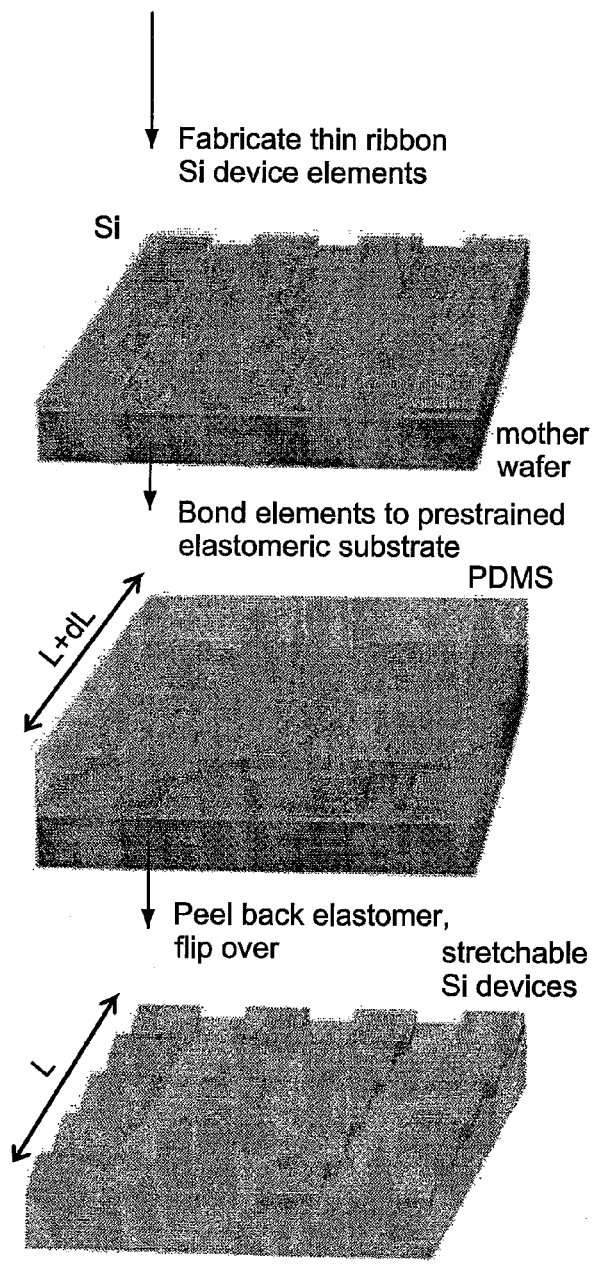
FIG. 14 illustrates a possible fabrication technique that can be utilized to make the circuits of FIGS. 6, 8 and 9 flexible and stretchable.

In the fabrication technique of FIG. 14, a stretchable single-crystal Si device is built on an elastomeric substrate. In the first step (top), thin (thicknesses between 20 and 320 nm) elements of single-crystal Si or complete integrated devices (transistors, diodes, etc.) are fabricated by conventional lithographic processing, followed by etching of the top Si and SiO$_2$ layers of a SOI wafer. After these procedures, the ribbon structures are supported by, but not bonded to, the underlying wafer. Contacting a prestrained elastomeric substrate (PDMS) to the ribbons leads to bonding between these materials (middle). Peeling back the PDMS, with the ribbons bonded on its surface, and then releasing the prestrain, causes the PDMS to relax back to its unstrained state. This relaxation leads to the spontaneous formation of well-controlled, highly periodic, stretchable wavy structures in the ribbons (bottom).

Those skilled in the art will appreciate that the fabrication techniques disclosed by J. Rogers et al. is advantageous in that the devices and circuits are fabricated on traditional silicon using standard SOI (silicon on insulator) processing techniques and in that very high performance devices, on par with standard silicon devices, are produced. Moreover, simple transfer mechanisms yield well-defined wavy silicon structures that are not only flexible, but stretchable as well. However, the development of 2-dimensional stretchable devices is in an early stage and could be expensive since such devices require one entire wafer of silicon per electrode array, including all of its traditional SOI processing steps, plus additional processing steps to make the silicon flexible.

Figure 15:
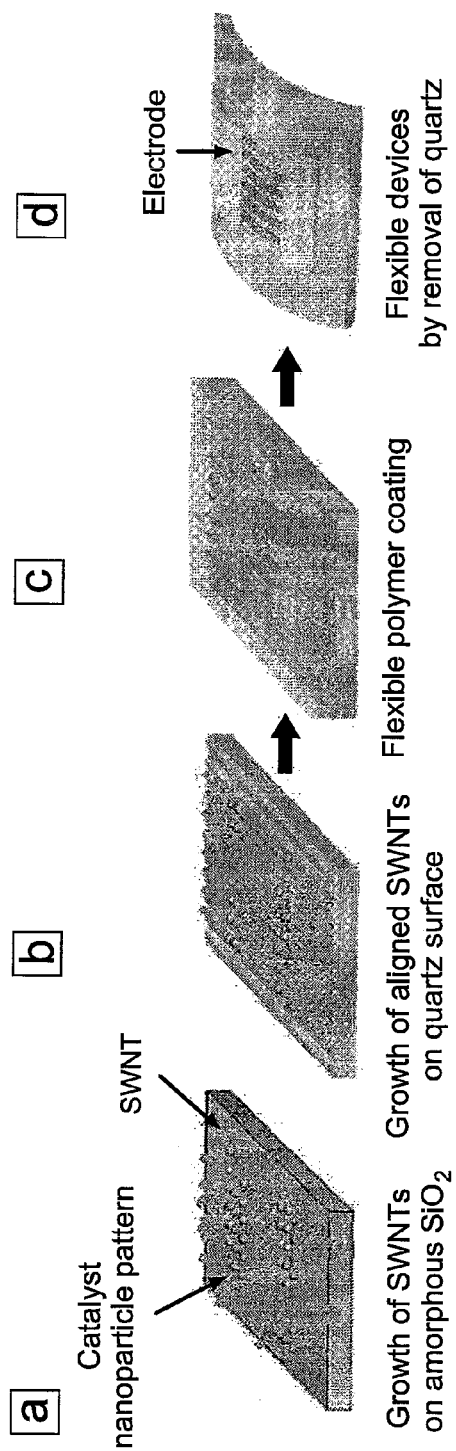
FIG. 15 illustrates a second technique for fabricating the electrode array of the invention.

Another method for fabricating the electrode arrays of the invention is provided by using single-walled nanotubes (SWNTs) (FIG. 15). As described by J. Rogers at the University of Illinois at Urbana-Champaign in an article by Hong et al., "A Flexible Approach to Mobility," Nature Nanotechnology, Vol. 2, April 2007, such an approach has the potential for very high performance flexible devices as SWNTs have carrier mobilities of ~10,000 $cm^2/Vs$, which is about 10× better than silicon. The performance of such single-walled nanotubes is described by Zhou et al. in "Band Structure, Phonon Scattering, and the Performance Limit of Single-Walled Carbon Nanotube Transistors," *P. Phys. Rev. Lett.*, Vol. 95, 146805 (2005).

In the fabrication technique of FIG. 15, a flexible electronic device is made by growing randomly orientated single-walled carbon nanotubes on an amorphous SiO2 surface (a) and then growing dense aligned nanotubes on a quartz crystalline surface (b). These steps are followed by the direct transfer of the nanotubes onto flexible substrates by flexible polymer coating (c) and removal of the quartz (d) to produce flexible, high-performance, high-power electronic devices. However, this technology is still in its early stages, and only single devices have been fabricated to date. Lithography techniques are needed to make complex circuits.

Figure 16:
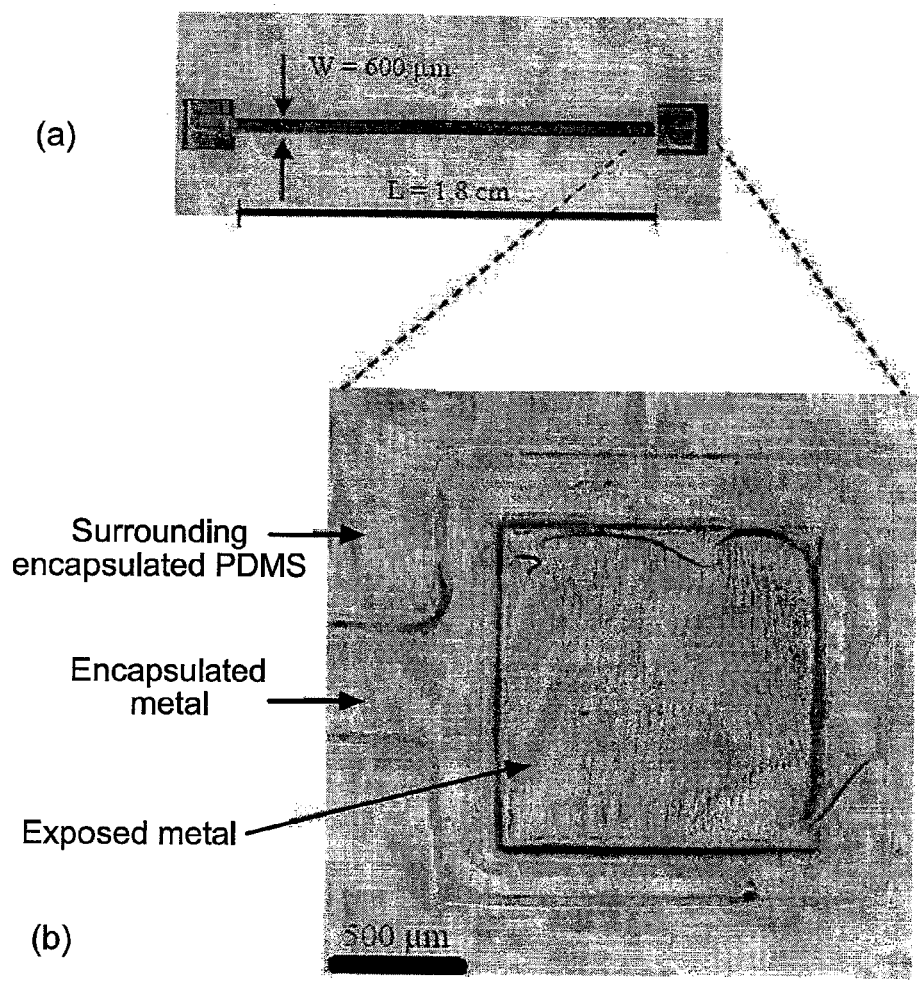
FIG. 16 illustrates a third technique for fabricating the electrode array of the invention.

In accordance with another possible fabrication technique, thin gold films are provided on elastomeric silicone substrates to form stretchable microelectrode arrays (FIG. 16). Such an approach is described by S. Wagner at Princeton in articles by Lacour S & Wagner S. entitled "Thin film transistor circuits integrated onto elastomeric substrates for elastically stretchable electronics, *Electron Devices Meeting,* 2005. *IEDM Technical Digest. IEEE International* (2005), pp. 101-104, and by Tsay C, Lacour S, Wagner S & Morrison B. entitled "Architecture, fabrication, and properties of stretchable micro-electrode arrays," *Sensors,* 2005 *IEEE* (2005), pp. 1169-1172. Such fabrication techniques are desirable as they have been demonstrated as a viable bio-compatible process for a stretchable micro-electrode.

In the fabrication technique of FIG. 16, an encapsulated electrode is formed on PDMS (FIG. 16a). As shown in FIG. 16b, exposed metal is surrounded by encapsulated metal which is surrounded by encapsulating PDMS. The exposed metal forms a contact in the clear encapsulation silicone over the metal pad. However, the resulting active elements are relatively slow and bulky. For example, a thin-film transistor (TFT) inverter only managed 500 Hz operation.

Figure 17:
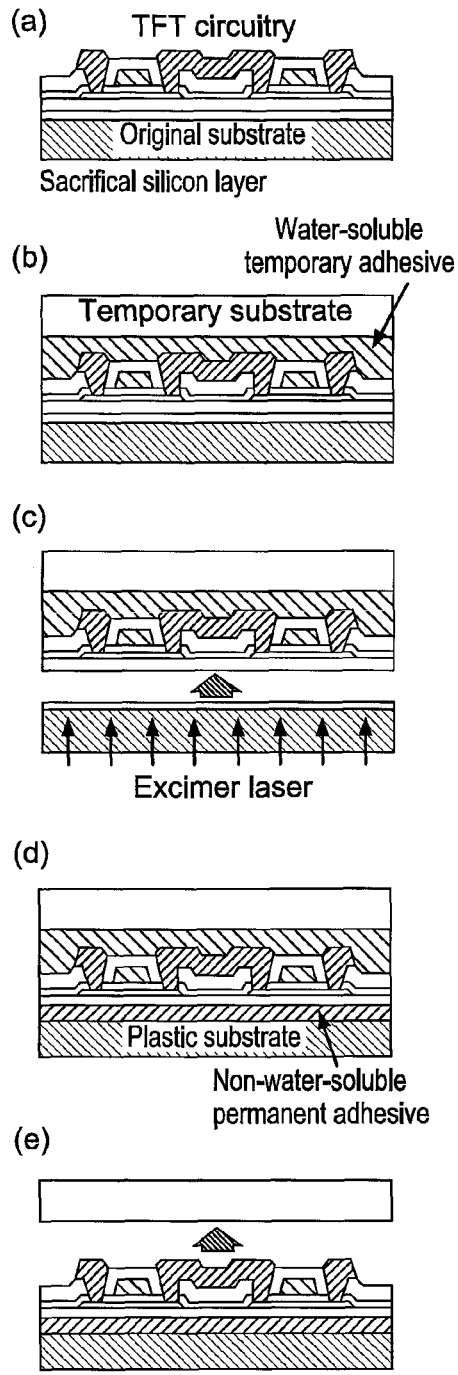
FIG. 17 illustrates a fourth technique for fabricating the electrode array of the invention.

Finally, in accordance with yet another possible fabrication technique, surface-tree technology by laser annealing (SUFTLA) developed by Epson Corporation may be used (FIG. 17). Such technology is described by Boyd in "Epson Takes Major Step Toward Flexible Electronics," Technology Newsline, No. 13, May 2005. As described in the Boyd article, such a fabrication technique is a low cost, large surface area TFT process through which complex circuits have been successfully fabricated. However, this fabrication technique produces relatively low performance devices with unpredictable propagation delays. Also, the resulting array is flexible, but not stretchable.

Implantation Techniques and Extensions

The implantable arrays described above may be deployed endoscopically or through some other means, such as through surgery (preferably minimally invasive). If the array is small, it may be implanted directly as a result of its small footprint. On the other hand, the flexible substrate may be rolled up for introduction and unrolled, unfurled or otherwise expanded once inside the body. On the other hand, the flexible substrate may be placed into the body as part of a vascular stent deployable within the body or as an integral part of a catheter system that is placed within vessels or organs, around peripheral or cranial nerves, and on, in or around other structures of the body.

Those skilled in the art also will readily appreciate that many additional modifications are possible in the exemplary embodiment without materially departing from the novel teachings and advantages of the invention. For example, a reshaped version of the disclosed electrode arrays may be used to increase the spatial sampling of current depth implantable electrode designs as well. The circuits would be wrapped around the barrel of the electrode body, allowing amplification and multiplexing throughout the length of the depth electrode. This would greatly improve the number of microelectrodes that can be placed in deep brain structures, such as the hippocampus, amygdala, and the anterior nucleus of the thalamus. The array of sensors also may be formed into a hollow or solid cylindrical shape to be implanted into a deep brain structure, wrapped around a nerve bundle or auditory nerve, a blood vessel, a peripheral or cranial nerve, or provided outside or inside a viscus or in or around the heart or eye. On the other hand, the array of electrodes may be formed into a device suitable for cardiac implantation or for recording from and applying stimulation to peripheral or cranial nerves, a spinal cord, a heart, a viscus or other biological target in a patient. The sensor array also may be disposed in a chamber in which biological material removed from the body is placed, and the array or sensors in such an embodiment would record from or monitor activity from the biological materials after removal from the body. The sensor array could be powered via wires, batteries (single use or rechargeable), through wireless power (inductive coupling), or some combination of those. Accordingly, any such modifications are intended to be included within the scope of this invention as defined by the following exemplary claims.

What is claimed is:

1. A method of introducing a sensor and/or effector array into tissue of a patient, comprising the steps of:
    forming an array of sensors and/or effectors arranged in a two-dimensional grid on a flexible substrate adapted for implantation into tissue of the patient;
    rolling up said flexible substrate around introducing means;
    using said introducing means to implant said flexible substrate within tissue of the patient; and
    unfolding or unfurling said flexible substrate at an implantation position.

2. A method as in claim 1, wherein said introducing means comprises an endoscope, a vascular stent, or a catheter, wherein using said introducing means comprises manipulating said endoscope, vascular stent, or catheter inside the patient's body to enable placement of the flexible substrate inside vessels or organs, around peripheral or cranial nerves, or on, in or around other structures within the patient's body.

3. A method as in claim 1, comprising the further step of deploying said flexible substrate within the tissue of the patient through surgery.

4. A method as in claim 1, wherein said switches comprise analog or digital switches arranged between adjacent sensors and/or effectors, further comprising selectively opening or closing said switches in response to logic to selectively connect the respective adjacent sensors and/or effectors to each other.

5. A method as in claim 4, further comprising connecting a plurality of sensors and/or effectors by said switches to form a macrosensor.

6. A method as in claim 1, further comprising providing configuration and control signals by wire or wirelessly to said switches.

7. A method as in claim 6, wherein said configuration and control signals are provided to said switches by a processor incorporated into the flexible substrate.

8. A method as in claim 7, further comprising tracking a position of respective sensors and/or effectors and identifying migration of said sensors and/or effectors within tissue using an algorithm executing on said processor.

9. A method as in claim 1, wherein arranging said switches between adjacent sensors and/or effectors comprises providing a set of multiplexing switches arranged in rows and columns.

10. A method as in claim 1, wherein said sensors and/or effectors comprise electrodes, optical sensors, chemical sensors, force sensors, and/or temperature sensors.

11. A method as in claim 1, further comprising amplifying and digitizing signals detected by said sensors and/or effectors using an amplifier and an analog to digital converter incorporated into said flexible substrate.

12. A method as in claim 1, further comprising providing a buffer amplifier at each sensor and/or effector and incorporating each buffer amplifier into said flexible substrate.

13. A method as in claim 1, further comprising incorporating into said flexible substrate an output amplifier that receives and amplifies the outputs of all sensors and/or effectors.

14. A method as in claim 1, wherein forming said array of sensors and/or effectors comprises incorporating at least 100×100 sensors and/or effectors in an area of said flexible substrate no greater than 36 cm$^2$.

15. A method as in claim 1, further comprising sampling a large number of sensors and/or effectors simultaneously.

16. A method as in claim 1, wherein said forming step comprises forming said array of sensors and/or effectors into a hollow or solid cylindrical shape adapted to be implanted into a deep brain structure, wrapped around a nerve bundle or auditory nerve, a blood vessel, a peripheral or cranial nerve, or provided outside or inside a viscus in or around a heart or eye.

17. A method as in claim 1, wherein said forming step comprises forming said array of sensors and/or effectors into a device adapted for cardiac implantation or for recording from peripheral or cranial nerves, a spinal cord, a heart, a viscus or other biological target in a patient.

18. A method as in claim 17, wherein said device comprises a stent, and the method further comprising deploying said stent within a patient's body.

19. A method as in claim 1, further comprising providing power to said array of sensors and/or effectors from at least one source outside of a patient's body.

* * * * *